United States Patent [19]

Kanca, III

[11] Patent Number: 4,666,406

[45] Date of Patent: May 19, 1987

[54] PHOTOCURING DEVICE AND METHOD

[76] Inventor: John Kanca, III, 390 Middlebury Rd., Middlebury, Conn. 06762

[21] Appl. No.: 570,380

[22] Filed: Jan. 13, 1984

[51] Int. Cl.$^4$ .............................................. A61C 5/00
[52] U.S. Cl. .................................... 433/229; 433/215; 433/228.1; 350/96.10
[58] Field of Search ............... 350/96.10, 96.24, 96.25, 350/96.26, 96.27, 96.28, 96.29, 96.30; 362/32; 433/2, 3, 25, 172, 180, 190, 192, 202, 212, 215, 226, 229, 228; 128/630, 633, 634, 636

[56] References Cited

U.S. PATENT DOCUMENTS

| | | | |
|---|---|---|---|
| 2,843,112 | 7/1958 | Miller | 350/96.26 |
| 3,265,881 | 8/1966 | Hovanian et al. | 350/96.26 |
| 3,335,715 | 8/1967 | Hugenholtz | 128/634 |
| 4,298,806 | 11/1981 | Herold | 250/504 H |

FOREIGN PATENT DOCUMENTS 2028994 3/1980 United Kingdom .................. 433/25

Primary Examiner—Robert Peshock
Attorney, Agent, or Firm—Lawrence Hager

[57] ABSTRACT

A light delivery device and resin curing method to facilitate access to and improved curing of composite material applied, for example, to posterior teeth cavity preparations. The light delivery or photocuring device basically comprises a fibre optic wand having a slender rod shaped or needle like fibre optic tip or end cap. Improved photocuring may be effected with the light transmitting fibre optic tip being placed and/or oscillated juxtaposition with the light curable resin deposited within a tooth cavity.

7 Claims, 8 Drawing Figures

PHOTOCURING DEVICE AND METHOD

FIELD OF INVENTION

The present invention relates to light curing devices and methods utilized in the dental profession for curing resin cavity fillings.

BACKGROUND OF THE INVENTION

Fibre optic light devices such as is described in U.S. Pat. No. 4,298,806 have been used in the dental profession for several years.

Typically, the prior art light device comprised a fibre optic wand having a relatively large end portion which is held above or at the biting crown surface of, for example, posterior teeth such as bicuspids and molars, with the light being directed inwardly generally in the direction of a light activatable resin filling within a cavity preparation. A principal disadvantage and shortcoming of the prior art light units and curing procedure is the fact that the end of the wand and, therefore, the light source is held distal from the resin filling which may result in insufficient depth of curing and/or incomplete exposure of portions of the resin surface to the light due to the location of the cavity preparation. This has typically occurred with treatment of recessed cavity preparation such as within or about the dentin, pulp or cementum regions.

In contrast to the prior art, the present invention provides a light device or attachment and a dental procedure to enable improved photocuring of a resin type filling within a tooth cavity, and the ability to light expose such fillings within recessed and side wall cavitations in a tooth. The light device or attachment, generally speaking, comprises a source of light provided through a fibre optic wand or hand piece having a slender rod or needle shaped tip or end cap adaped to enable it to be inserted into a cavity preparation and/or between adjacent teeth and like relatively small alcoves or recesses. The photocuring procedure is effected by disposing the fibre optic rod or tip in juxtaposition with the resin type filling while shining or providing light therefrom. The rod or tip may be oscillated or moved about or over the exposed surface portion of the resin filling to enhance and improve the uniformity of its surface and/or depth of subsurface curing.

SUMMARY OF THE INVENTION

A light device having particular utility in the dental profession, in combination comprising:

a light generating means (18) having a fibre optic wand (12) for providing light from an end portion (13) thereof;

cap means (26) having a fibre optic rod or similar thin light guidance means (30), said cap means being configured for being readily manually mountable onto and removable from the end portion of said wand, said rod or light guidance means dimensioned for being insertable into a cavity preparation or boring or between adjacent teeth for providing a source of light thereat.

A method or dental procedure for light curing a composite resin disposed within a cavity preparation of a tooth, comprising the steps of:

placing a relatively thin or small diameter fibre optic rod or light conduit means (30) into a boring or a cavity preparation or between adjacent teeth;

disposing said rod or light conduit means proximate with a portion of the composite resin;

shining light via said rod or light conduit means on a portion of the composite resin;

whereby the composite resin being exposed to a proximate curing light.

Another feature of the inventive method or dental procedure includes the additional step of:

oscillating or moving about the fibre optic rod or light conduit means over the surface of the composite resin filling to improve depth of curing and/or to cure the composite resin at recessed tooth locations not otherwise readily curable by luminescing from atop the crown portion of the tooth being treated.

Accordingly, it is an object of the present invention to provide a new and improved light curing device for application with a light curable composite resin.

A further object of the invention is to provide a new attachment cap or head for a dental light curing unit.

A further object of the invention is to provide a light guidance or conduit means for improving the depth of cure of composite resin fillings within a cavity preparation.

A further object of the invention is to provide a light means for being insertable between adjacent teeth or within a recessed boring or cavity preparation.

A further object of the invention is to provide a new and improved attachment device for dental light curing units/systems.

A further object of the invention is to provide a new method of light curing composite resin material.

A yet further object of the invention is to provide a new and improved dental procedure for effecting light curing of resin fillings within a cavity preparation.

BRIEF DESCRIPTION OF THE DRAWINGS

Other objects and advantages of the invention may be more clearly seen when viewed in conjunction with the accompanying drawings. Similar reference numerals refer to similar parts throughout.

DESCRIPTION OF THE PREFERRED EMBODIMENTS

Figure 1:
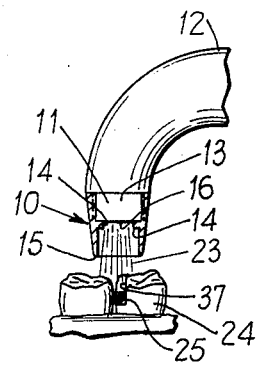
FIG. 1 is a side view, partly cutaway, of a prior art light unit shining light on a tooth.
Figure 2:
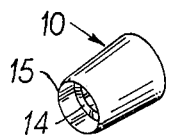
FIG. 2 is a perspective view of the end cap shown in FIG. 1.

In order to give better understanding of the present invention, a brief description will first be made of a prior art dental light device having a wide end cap 10 as shown in FIGS. 1 and 2.

Typically, end cap 10 is force-fitted or snapped over the end 11 of a fibre optic wand 12. Fibre optic wand 12, which may be of conventional design, includes an internal elongate fibre optic bundle (not shown) having a relatively wide diameter exposed or projecting tip portion 13. Cap 10 has an internal circumferential ledge 14. Ledge 14 is recessed inwardly from rim 15 of cap 10, and may be configured to abut the bottom edge 16 of the fibre optic tip 13.

Figure 3:
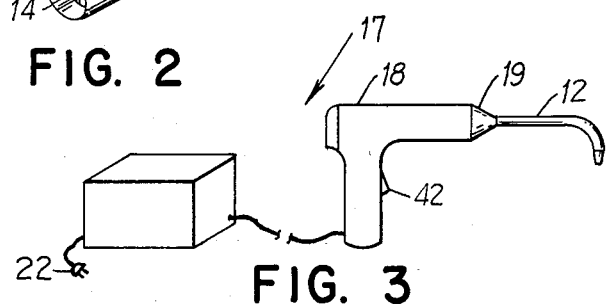
FIG. 3 is a perspective view of a dental light unit.

Cap 10 is typically used in conjunction with a light unit or system 17 as illustrated in FIG. 3. Light unit 17 may be of conventional design. Typically, light unit 17 comprises a handpiece 18 having a nozzle 19 for receiving an end 20 of fibre optic wand 12, and a power unit 21 which is connected to a wall outlet (not shown) via plug 22.

With cap 10 mounted on wand end 11, the light 23 emitting wand 12 is inserted into a dental patient's mouth and held above or next to the crown of the treated tooth 24 as shown in FIG. 1. The light 23 being emitted from the bottom 16 of the fibre optic wand 12 is used to cure the composite resin filling 25. The composite resin 25 may be a conventional gel like material such as is available from Teledyne Getz and referred to as a Light Activated Restorative, or a 3M Company product named SILUX. However, as noted above and as can be readily seen from FIG. 1, the source of the emitting (curing) light, i.e., the bottom 16 of wand 12, is held distal from the light cured composite resin 25. This is necessitated by the wide or large dimension of cap 10 and by the intermediate recessing of the bottom end 16 within cap 10. It should be appreciated that this distal spacing of the light source from the light activated resin filling 25 may adversely affect the depth of cure of the filling 25.

Figure 4:
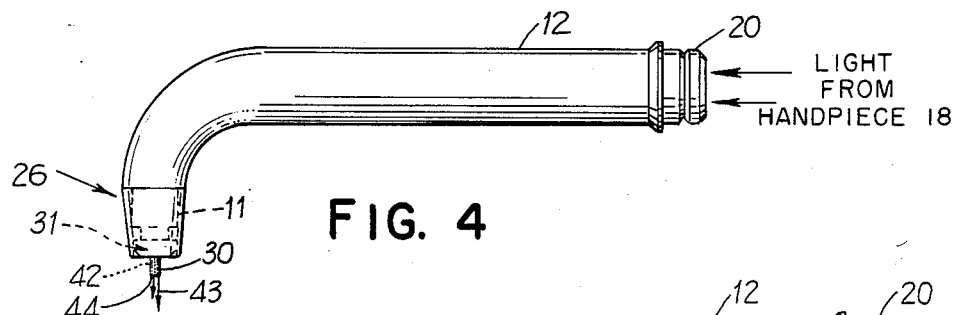
FIG. 4 is a side view of a fibre optic wand and cap attachment in accordance with the present invention.
Figure 5:
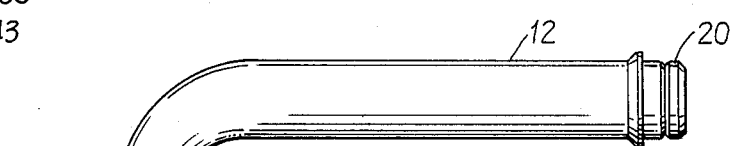
FIG. 5 is an exploded view of the wand and cap attachment shown in FIG. 4.
Figure 6:
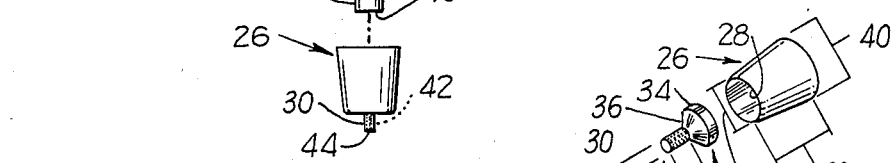
FIG. 6 is an exploded view of the cap attachment shown in FIGS. 4 and 5.

With reference now to FIGS. 4, 5 and 6, a new and improved attachment or fibre optic cap 26 is shown in accordance with the present invention. Fibre optic wand 12 is shown detached from handpiece 18 for ease of illustration. Fibre optic cap 26 has a tapered circular configuration with a hollow interior or wand receiving alcove 27.

Fibre optic cap 26 may be formed of plastic or other suitable material and has an opening 28 extending into interior cavity 27. Opening 28 has a circular configuration with a diameter approximately equal to or greater than the diameter of the projecting fibre optic tip 13. A fibre optic extension member 29 is affixed to cap 26. Extension member 29 basically comprises a fibre optic glass like rod 30 having a generally circular shaped upper fibre optic brim or contoured lense or focusing member 31. Rod 30 and brim 31 may be integrally formed or affixed together to form a light conduit or guidance means. Rod 30 generally has an elongate circular configuration with a diameter 32 approximately between two and four millimeters and a length 33 approximately between three and eight millimeters. In accordance with the preferred embodiment of the invention, rod 30 has a diameter or thickness of three millimeters and a length of five millimeters. Focusing member 31 generally has a disk like configuration with a diameter slightly less than the diameter of opening 28, and configured for being inserted into and affixed, for example, epoxied, to the side walls forming opening 28 about its periphery or edge 34. The thickness of focusing member 31 and, therefore, edge 34 may be selected such that its upper substantially flat surface portion 35 extends within cavity 27 a predetermined distance for being abutted with or juxtaposed to a mating bottom 16 portion of fibre optic bundle or rod 13, with cap 26 being placed about the tip 11 of wand 12. Alternatively, cap 26 may be dimensioned to provide an intermediate space between top or upper portion 35 and the bottom surface 16 of rod 13 if manufacturing constraints require same. The lower portion 36 has a contoured or sloped outer surface to enhance light focusing within fibre optic rod 30. Other conventional focusing techniques may be utilized to enhance light transmission between fibre optic wand 12 and rod 30.

Figure 7:
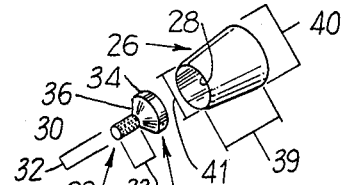
FIG. 7 is a perspective back view of the cap attachment.

Cap 26 has a generally tapered configuration with a length 39 of approximately twelve millimeters, an upper diameter 40 of approximately twelve millimeters, and a bottom diameter 41 of approximately ten millimeters. The upper portion of cap 26 has an opening extending into and forming part of cavity 27 as can be seen from FIG. 7. Cavity 27 is configured and dimensioned for receiving tip 11 and rod 13 therein.

As noted above, cap 26 is adapted for being placed over tip 11 (as shown in phantom outline in FIG. 4) such that the bottom flat surface 16 of the fibre optic bundle or rod 13 abuts or juxtaposes with the upper flat surface 35 of the fibre optic extension member 29.

Figure 8:
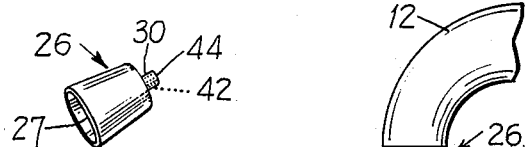
FIG. 8 is a perspective view of the fibre optic wand and cap attachment being utilized to light cure a resin filling in accordance with the present invention.

With reference now to FIG. 8, the method or dental procedure for curing composite resin fillings will now be described. Cap 26 is placed securely on the end of wand 12 (as shown in FIG. 4) and wand 12 is inserted at end 20 into the nuzzle 19 of light gun or handpiece 18 (as shown in FIG. 3). A cavity preparation 37, for example, in posterior tooth 24, is filled to an appropriate height with a light activatable composite resin 25. Such resins are commercially available. Next, with light gun 18 being held by the dentist, wand 12 is inserted into the patient's mouth (not shown). The light gun 18 is then manipulated by the dentist (not shown) such that fibre optic extension rod 30 is inserted into the cavity preparation or drilling in the general proximity of the composite resin filling 25. When the dentist has properly positioned the fibre optic extension rod 30 as shown in FIG. 8, light gun 18 is activated, for example, by trigger 42, to thereby effect the provision of a resin curing light, via light gun 18, wand 12, light focusing member or disk 31 and extension rod 30, onto resin 25. As noted above, wand 12 may be manipulated by the dentist to shine or provide the curing light, via light source rod 30, over all or a substantial portion of the exterior surface(s) of the resin filling 25.

The localized light source or extension rod 30 may also, if teeth spacing permits, be inserted between adjacent teeth 24 and 38 to enable the shining of the curing light on the side wall portion of the resin filling 25.

It should now be appreciated and understood that the depth of cure and/or control of a localized filling surface(s) exposure to a curing light is substantially facilitated and improved with the above described method of curing dental fillings in accordance with the present invention. It should also be appreciated that rod 30 may be coated 42 about its elongate round exterior surface to confine and, thereby, direct the light 43 from without its lower tip 44.

While there has been shown what is considered to be the preferred embodiment of the invention, it is desired to secure in the appended claims all modifications as fall within the true spirit and scope of the invention. For example, rod 30 may comprise a curved elongate rod shaped member or other configurations designed to meet particular needs. It being understood that the concept would remain substantially similar to that of the present invention, i.e., to provide a light source or conduit and procedure for enabling the relatively proximate delivery/application of a curing light to composite resin fillings.

I claim:

1. An attachment device for a fibre optic wand like dental instrument having particular utility for curing a light activated/cured composit resin type filling within a tooth cavity preparation, comprising:

a somewhat thimble-shaped cup and a fibre optic extension member, said cup defining a wand receiving chamber dimensioned to fit about a fibre optic end member of the wand and having an opening at a bottom wall member of said cup member extending into said wand receiving chamber, said fibre optic extension member having a disc shaped upper member affixed within a portion of the bottom opening of said cup member with a top surface portion being exposed within said wand receiving chamber and having a downwardly projecting fibre optic rod member dimensioned for being insertable within the cavity preparation.

2. An attachment device as in claim 1, wherein:

the cup member has a tapered exterior surface and is formed of plastic, the fibre optic extension member is integrally formed of a fibre optic material and as an opaque coating about a portion of its exterior surface for defining a light transmission path from said top surface portion to an end portion of said rod member.

3. A light device as in claim 1, wherein: the fibre optic rod member has a length between three millimeters and eight millimeters and a diameter between two millimeters and four millimeters.

4. A light device as in claim 1, wherein: the fibre optic rod member has a straight round elongate bar configuration.

5. A light device as in claim 1, wherein: the fibre optic rod member has a curved bar configuration.

6. A method for light curing a composit resin type filling within a tooth cavity preparation with the use of a hand-held type light source having a projecting fibre optic wand, comprising the steps of:

attaching a fibre optic extension means having a relatively thin elongate rod shaped member onto the wand;

disposing a portion of said rod shaped member within the tooth cavity preparation in relatively close proximity with the composit resin filling; and activating the light source to provide light via the wand and said fibre optic extension means onto a portion of the composit resin filling whereby the composit resin being exposed to a substantially proximate curing light source.

7. A method for light curing a composite resin type filling as in claim 6, including the steps of: vibrating the fibre optic extension means while a portion of said rod member is maintained in juxtaposition with the surface of the composite resin such that light is shined over a substantial portion of the surface of the composite resin for effecting curing thereof to a relatively greater depth.

* * * * *